United States Patent
Wang et al.

(10) Patent No.: US 9,226,967 B2
(45) Date of Patent: Jan. 5, 2016

(54) CHELATING COMPLEX MICELLES DRUG CARRIER

(71) Applicant: Original BioMedicals Co., Ltd, Tainan (TW)

(72) Inventors: Chau-Hui Wang, Kaohsiung (TW); Chia-Hung Chen, New Taipei (TW); Johnson Lin, Taipei (TW); Jing-Yi Chen, Taipei (TW); Wei-Chuan Liao, Kaohsiung (TW)

(73) Assignee: ORIGINAL BIOMEDICALS CO., LTD, Tainan (TW)

( * ) Notice: Subject to any disclaimer, the term of this patent is extended or adjusted under 35 U.S.C. 154(b) by 0 days.

(21) Appl. No.: 14/306,667

(22) Filed: Jun. 17, 2014

(65) Prior Publication Data

US 2014/0296451 A1 Oct. 2, 2014

Related U.S. Application Data

(62) Division of application No. 13/683,482, filed on Nov. 21, 2012, now Pat. No. 8,785,569.

(60) Provisional application No. 61/562,663, filed on Nov. 22, 2011.

(51) Int. Cl.
  *A61K 47/48* (2006.01)
  *C08G 81/00* (2006.01)
  *A61K 31/661* (2006.01)

(52) U.S. Cl.
  CPC .......... *A61K 47/48076* (2013.01); *A61K 31/661* (2013.01); *A61K 47/482* (2013.01); *A61K 47/488* (2013.01); *A61K 47/48015* (2013.01); *A61K 47/48192* (2013.01); *A61K 47/48215* (2013.01); *C08G 81/00* (2013.01)

(58) Field of Classification Search
  CPC ................. A61K 47/48215; A61K 47/48076; A61K 47/482; A61K 9/51; C08G 2261/126
  See application file for complete search history.

(56) References Cited

U.S. PATENT DOCUMENTS

| | | | | |
|---|---|---|---|---|
| 7,138,105 | B2 * | 11/2006 | Bolotin | 424/9.36 |
| 7,189,705 | B2 * | 3/2007 | Lam et al. | 514/44 R |
| 2005/0196343 | A1 * | 9/2005 | Reddy et al. | 424/9.322 |
| 2007/0148125 | A1 | 6/2007 | Kataoka et al. | |
| 2007/0154396 | A1 * | 7/2007 | Wang et al. | 424/9.34 |
| 2007/0154398 | A1 * | 7/2007 | Wang et al. | 424/9.34 |
| 2011/0123458 | A1 | 5/2011 | Kataoka et al. | |
| 2013/0071482 | A1 * | 3/2013 | Bae et al. | 424/497 |

FOREIGN PATENT DOCUMENTS

| | | |
|---|---|---|
| CN | 1890295 A | 1/2007 |
| CN | 102026625 A | 4/2011 |
| JP | 2011105792 | 6/2011 |
| JP | 2011105792 A * | 6/2011 |
| JP | 2011205792 A | 10/2011 |
| KR | 928294 B1 * | 11/2009 |
| WO | 0110468 | 2/2001 |
| WO | 2012058552 | 5/2012 |

OTHER PUBLICATIONS

Jang et al. "The multimetal—co-ordinate bond composite micelle, and the manufacturing method thereof and pharmaceutical composition including the same." KR 928294B1, Nov. 25, 2009, English machine translation.*
Oerlemans et al. "Polymeric Micelles in Anticancer Therapy: Targeting, Imaging and Triggered Release" Pharm. Res. 2010, 27, 2569-2589.*
Huh et al. "Hydrotropic polymer micelle system for delivery of paclitaxel" J. Controlled Release 2005, 101, 59-68.*
Malmsten, M., "Micelles" and "Liposomes" in Surfactants and Polymers in Drug Delivery (New York, CRC Press, 2002), chapters 2 and 4.
Kataoka et al. "Block copolymer-metal complex composite, hollow structure carrier containing the composite, composition and containing the carrier, and its use for cancer treatment and diagnosis" JP2011105792—(Machine Translation: English) Jun. 2, 2011.
Kataoka et al. JP 2011/105792 A, published Jun. 2, 2011—Partial English translation provided Jul. 29, 2013 by Steven Spar of the U.S. Patent and Trademark Office Translation Service Center, Alexandria, VA.
Yokoyama, M. "Clinical Applications of Polymeric Micelle Carrier Systems in Chemotherapy and Image Diagnosis of Solid Tumors", Journal of Experimental and Clinical Medicine ( Jun. 2011) doi:10.1016/j.jecm.2011.06.002.

* cited by examiner

*Primary Examiner* — Joseph Kosack
*Assistant Examiner* — Amanda L Aguirre
(74) *Attorney, Agent, or Firm* — WPAT, PC; Justin King

(57) ABSTRACT

This invention provides Chelating Complex Micelles as a drug carrier. The Chelating Complex Micelles can load drugs without changing their structure, and therefore extend the half-life of drugs in the human body. The chelating complex micelles contain a metal ion core, at least one polymer, and at least one drug molecule. The metal ion is considered as a Lewis acid while polymer chain and drug molecules are referred to as Lewis bases. The drug molecule is linked to the polymer via forming coordinate bonds with metal ion, and then self-assembled to form chelating complex micelles as a drug carrier.

6 Claims, 6 Drawing Sheets

CHELATING COMPLEX MICELLES DRUG CARRIER

CROSS REFERENCE TO RELATED APPLICATIONS

This is a divisional of U.S. Ser. No. 13/683,482, filed Nov. 21, 2012 by the same inventors, and claims priority there from. This divisional application contains rewritten claims to the restricted-out subject matter of original claims.

FIELD OF THE INVENTION

The present invention is a drug carrier, in particular, a chelating complex micelle drug carrier, and its formation and formulation.

BACKGROUND OF THE INVENTION

Adverse effects, occurred in cancer patients receiving radiation therapy and chemotherapy, are well known. The toxicity of anticancer therapy has always been a major concern of patients because such therapy causes serious adverse effects. For patients who cannot complete the intended course of treatment, the therapy not only fails to achieve the desired and predicted outcome but the medical resources are also wasted. Because of its relatively non-selective action on both normal and cancer cells, radiation therapy and chemotherapy not only eliminate cancer cells but may also kill normal cells. Common adverse effects for patients receiving these treatments include oral ulcers, loss of appetite, diarrhea, hair loss, and a decrease of white blood cells and platelets, which can lead to other fatal complications. Adverse effects often limit the therapeutic dosages administered, and hence the therapeutic efficacy; part of the adverse effects can be reduced by changing drug delivery, such as dividing the doses or increasing the administration duration or local administration. Examples of the latter include intraperitoneal or intra-arterial chemotherapy, which limits the systemic adverse effects by confining high concentrations of drugs to the lesion sites; or administering antagonists (or antidotes) after the drugs have exerted their therapeutic effects, which may reduce the toxic effects of anticancer drugs on normal cells. However, the above approaches are not selective, and there is only a marginal decrease in the toxicity to normal cells; moreover, the therapeutic efficacy on cancer cells is also compromised. The alternative approach is to treat the adverse effects immediately after drug administration to minimize the harmful effects, such as administering white blood cell growth factors and potent antiemetic agents; however, this approach only partially reduces the existing adverse effects, and lacking preventive effects. It is impossible to have a drug exhibiting only therapeutic effect and no adverse effects. Furthermore, once the tumor is formed, relentless replication and growth of cancer cells will metastasize to distant organs via blood and lymphatic vessels, which may ultimately produce drug resistance cancer cells leading to treatment failure. Anticancer and radiation therapy are no longer effective in controlling tumor growth and spread. Accordingly, the focal point to consider in radiotherapy and chemotherapy is to attack cancer cells while concomitantly protect normal cells to reach the goal of radiotherapy and chemotherapy. Since the action mechanism of chemotherapy and radiation therapy is partially due to free radical damage, a rational selective utilization of substances possessing both antioxidant and free radical property can reduce the damage to normal cells under such treatment.

Amifostine (Ethyol; WR-2721) is a thiophosphate cytoprotective agent against radiation damage. It is a precursor of phosphorylated aminothiol, which is converted to an active free thiol metabolite, WR-1065, by alkaline phosphatase in the cells, body fluids and blood. WR-1065 can protect the cells from radiation and chemical damage, thereby protecting cancer patients from serious adverse effects caused by radiotherapy and chemotherapy. The alkaline phosphatase level in cancer cells is much lower than that of normal cell, and the condition of blood flow and the acidic environment surrounding cancer cells are also unfavorable for alkaline phosphatase. The tissue protective effect can combine with the active alkylating agents and platinum analogs to form thioether conjugates, which can prevent alkylating agents and platinum analogs from combining with the normal tissue DNA or RNA. In addition, WR-1065 can partially reverse the preformed endogenous DNA-platinum adduct assisting the removal of DNA-platinum, and allowing normal DNA to function. WR-1065 can also provide $H^+$ ion for the repair of DNA damage. WR-1065 is also a potent ROS (reactive oxygen species) scavenger. It can eliminate the ROS generated by radiation therapy and certain chemotherapeutic drugs to prevent cell damage. In in vitro, WR-1065 can effectively eliminate hydroxyl radical (OH)-related spin-trap signal, superoxide anion and doxorubicin-derived superoxide anion. The scavenging effect of WR-1065 on ROS can be used to prevent bleomycin induced pulmonary inflammation and fibrosis.

Amifostine can reduce the toxic effects and protect normal tissue from cancer chemotherapy; it can increase the effective dosage and response rate of chemotherapy and radiation therapy. In addition, amifostine when combined with other growth factors or cytokines can exert synergistic protection on hematopoietic stem cells. The cytoprotective effect of amifostine appears 5-10 minutes after injection with short blood half-life ($\beta t_{1/2}$=8.8 min), rapid plasma clearance with approximately 90% cleared within 6 minutes. Amifostine is rapidly distributed to various tissues, dephosphorylated, and reaches a steady state in about 10 minutes. In contrast, the distribution of amifostine to tumor tissue is much less and also slowly dephosphorylated to active metabolite. Following injection, the concentration of amifostine in normal cells, including kidney, lung, liver, skin, bone marrow, intestine and spleen, is 10 times that of cancer cells. Amifostine is much less distributed to brain tissue, skeletal muscle and tumor cells. Amifostine exerts selective protective effect on normal cells, but must be administered 15 to 30 minutes prior to chemotherapy or radiation therapy. However, routine treatment requires several hours, therefore, how to extend the half-life of amifostine in the human body becomes the major development target of the drug industry.

In addition to aforementioned amifostine, the half-life of usual dosage forms of drugs in the body is usually very short; following administration or injection into the body, these drugs may distribute to various tissues. In order to maintain a long period of action and effective drug distribution, higher dosages or multiple dosing beyond the effective blood concentration are necessary. However, administration of high dosages is toxic to body tissues and causes unnecessary adverse effects. To circumvent the shortcomings of conventional repeated dosing and to avoid overdose and waste of the drug, the DDS (drug delivery system) concept has been formulated to increase the efficacy of drugs and reduce the number of dosages. A commercially available carrier such as liposomes (or liposome capsule) is a spherical carrier which is formed by a single or multiple layers of phosphatidylcholine (PC). The structure constraints of these liposomes only permit it to carry hydrophilic drugs (in the inner core). These carriers are particularly prone to accumulating in the liver, very sensitive to temperature change, difficult to store, and not easy to transport in dry powder form (see C. Chen, D. Han, et al. (2010). "An overview of liposome lyophilization and its future potential." Journal of Controlled Release 142: 299-311).

Polymeric micelles demonstrate excellent potential as a drug carrier. The advantages include improved drug efficacy, improved protection and stabilization of drugs, reduced cytotoxicity, and better delivery to the intended targets. Furthermore, nano-scaled micelles have extended circulation time; far less effect or degradation from macrophage (mononuclear phagocyte system, MPS) and endoplasmic reticulum (reticular epithelial system, RES) system. Currently, it is the focus of drug delivery system (DDS). Polymeric micelles are commonly composed of amphiphilic block copolymers. In the aqueous solution, the polymer chains self-assemble to form the micelles with a core-shell structure, thus providing an excellent reservoir (inside the core) for hydrophobic drugs (such as: indomethacin, doxorubicin, amphotericin B). Using polymeric micelles to deliver drugs may also improve their stability and efficacy. Drugs can be loaded by polymeric micelles through physical encapsulation, chemical bonding or electrostatic interactions. The driving force of physical encapsulation is primarily the interactions between the hydrophobic segment of the polymer and the hydrophobic part of the drug. The chemical bonding uses covalent bond to link drug molecule to polymer, such as amide bond, which is very stable, less susceptible to enzyme degradation or hydrolysis. A spacer that can be broken down under specific condition must be introduced between the drug molecule and the polymer chain to facilitate the release of the drug molecule. The physical forces only limit to encapsulate hydrophobic drugs; drugs loaded through chemical bonding requires complicated synthetic steps, thus resulting in lower loading rate.

In addition to physical encapsulation and covalent bonding mentioned in the previous section, electrostatic interaction has also been attempted in polymeric micelles. For this, the polymers are designed so that one end segment is undissociated while the other end is ionizable. In the appropriate medium, the ionizable segments interact with oppositely charged drugs, thus forming polyion complex micelles (PIC micelles) with core-shell structure. However, the use of electrostatic force to carry drugs also has limitations. The drugs with low molecular weight or high water-solubility are easily displaced by the ions in solution. Another approach is direct bonding of drugs to the carriers, especially metal-containing drugs such as cisplatin, carboplatin, or oxaliplatin. However, these metal-containing drugs are taken as Lewis acids, and its functional groups will be replaced when bound to carriers. The alteration of structure is considered as a new drug, which necessitates reevaluating the safety and efficacy. This may lead to a significant increase in cost. Accordingly, developing a new drug delivery carrier is the major target that the industry desperately needs.

SUMMARY OF THE INVENTION

From the background information presented above and to accommodate the special needs of the industry, the present invention provides a chelate-type drug carrier with coordination bonds to address the unmet objectives encountered in the conventional technology.

The aim of the present invention is to provide a drug carrier containing a metal ion core. This carrier comprises a metal (including transition metals) at the center (i.e., metal core), which interacts with the polymer (including block copolymers) possessing chelating ligands to form the coordinate bonds. Drugs that can donate a lone pair of electrons (including drugs possessing functional groups, such as carboxylic acids, alcohols, ketones, furans, amines, anilines, pyrroles, thiols, esters, amides, imines, pyridines, pyrimidines, imidazoles, pyrazols, sulfonamides, phosphonic acids, etc.) can also bind to metal center through coordinate bonds, which then form a complex, or chelating complex micelles (CCM) with the polymer containing chelating ligands. The coordinate bond (also known as dipolar bond) is a special kind of covalent bond in which the two electrons derive from the same atom. The formation of coordinate bond requires two conditions: first, the metal ion must have an incomplete octet of electrons; and second, the ligand donates a lone pair of electrons. Typically, a coordinate bond is formed when a Lewis base donates a pair of electrons to a Lewis acid. In reality the atoms carry fractional charges; the more electronegative atom of the two involved in the bond will carry a fractional negative charge.

The preparation of present invention, chelating complex micelles (CCM), is much easier than the physical encapsulation and chemical bonding of drugs. Physical encapsulation that requires large quantities of organic solvents is limited to encapsulate hydrophobic drugs due to the intrinsic property of block copolymer. On the other hand, drugs loaded via chemical bonding exhibit the shortcoming of insufficient loading capacity. In the present invention, the only requirement for the drug is to have a functional group that can donate a lone pair of electrons. The chelating complex micelles are formed when drugs and polydentate ligands bind to metal center at the same time. These micelles can carry not only hydrophobic but also hydrophilic drugs; thus, can be used extensively in the drug delivery systems.

Furthermore, besides providing a linkage between polymer and drug molecule, the following metal can be used for imaging analysis: gadolinium Gd(III) for MRI (magnetic resonance imaging), technetium $^{99m}$Tc for SPECT (single photon emission computed tomography), gallium $^{68}$Ga for PET/CT (positron emission tomography/computed tomography), rhenium $^{188}$Re for internal radiation therapy, and indium $^{111}$In for white blood cells magnetic resonance imaging. The application of this invention provides real-time monitoring techniques for imaging and therapy. Incorporation of targeting moiety, such as folic acid, into CCM will allow the accumulation of drugs in tumor tissues and accomplish the aim of selectively attacking cancer cells.

Another aim of the present invention is to provide a drug carrier loading with a cytoprotective agent. The carrier comprises a metal ion, which interacts with a cytoprotective agent (including amifostine, WR-1065) via coordinate bonds and at least one block copolymer (poly(ethylene glycol)-block-poly (glutamic acid); PEG-b-PGA) to form a chelating complex micelle. The carboxylic acid on PGA and phosphonic acid on amifostine provide lone pairs of electrons, thus forming coordinate bonds with metal. The PEG segments that without chelating ligands can extend outside the micelles, and therefore enhance their dispersity.

Accordingly, the chelating complex micelles of the present invention contain polydentate ligands and metal ions can carry both hydrophobic and hydrophilic compounds. The advantages of biodegradability, excellent dispersity in aqueous solution, real-time monitoring, and longer half-live of drugs will fulfill a much needed developmental target in the biomedical industry.

Based on the objectives stated in the preceding paragraphs, the present invention provides chelating complex micelles comprising a metal ion core, which acts like a Lewis acid, and at least one ligand, which interacts with the metal ion through the coordinate bond. The metal in the core is selected from the following list, including any combinations, or combinations of its derivatives thereof: Fe, Cu, Ni, In, Ca, Co, Cr, Gd, Al, Sn, Zn, W, Sc, Ti, Mn, Mg, Be, La, Au, Ag, Cd, Hg, Pd, Re, Tc, Cs, Ra, Ir, Ga, and combinations thereof. The ligand is selected from the compound possessing functional groups in following list, including any combinations, or combinations of its derivatives thereof: carboxylic acids, alcohols, ketones, furans, amines, anilines, pyrroles, thiols, esters, amides, imines, pyridines, pyrimidines, imidazoles, pyrazols, sulfonamides, and phosphonic acids.

The chelating complex micelles also contain a drug molecule, which act as Lewis base. The drug molecule interacts with the metal in the core through coordinate bonding. The drug molecule contains one or more functional groups, which can be selected from the following list including any combinations or combinations of its derivatives thereof: carboxylic acid, alcohols, ketones, furans, amines, anilines, pyrroles, thiols, esters, amides, imines, pyridines, pyrimidines, imidazoles, pyrazols, sulfonamides, phosphonic acids. The drug can be selected from the following list, including any combinations or combinations of its derivatives thereof: amifostine, WR-1065, doxorubicin, pemetrexed, gemcitabine, methotrexate, docetaxel, vinblastine, epirubicin, topotecan, irinotecan, ifosfamide, gefitinib, erlotinib, penicillin class, cloxacillin, dicloxacillin, gentamicin, vancomycin, amphotericin, quinolones, piperazine, fluoroquinolone, nalidixic acid, ciprofloxacin, levofloxacin, trovafloxacin, oseltamivir, metformin, trastuzumab, imatinib, rituximab, bevacizumab, celecoxib, etodolac, ibuprofen, cyclosporine, morphine, erythropoietin, granulocyte colony-stimulating factor, curcumin (enol, keto form), glutathione, Vitamin C, acetylcysteine, carnitine, galantamine, insulin, imipenem, cilastatin, ertapenem, meropenem, entecavir, telbivudine, lamivudine, melatonin, tocopherols, tocotrienol (Vitamin E), L-carnitine, carotenes, ubiquinol, lipoic acid, polyphenols, catecholamine, resveratrol, piceid, tempo, asarone, aminoguanidine, tocopherol monoglucoside, glycyrrhizic acid, epicatechin, flavonoid, orientin, vicenin, MPG (2-mercaptopropionyl glycine), and Mesna (2-mercaptoethanesulfonic acid).

Based on the objectives stated above, the present invention provides a chelating complex micelle drug carrier, which contains at least one polymer, at least one metal, and at least one drug molecule. The polymer and drug molecule, which act as Lewis base, link to metal Lewis acid via coordinate bonding. The selection criteria of metal and drug molecule are the same as the lists in preceding paragraphs. The polymers can be one of the following: unidentate ligands, bidentate ligands, tridentate ligands, hexadentate ligands, and polydentate ligands. The molecular weight of the polymer is around 1,000-100,000 Dalton, and is selected from the following list, including any combination or combination of its derivatives thereof: poly(ethylene glycol), poly(aspartic acid), poly(glutamic acid), poly(acrylic acid), chitosan, polyethyleneimine, poly(methacrylic acid), hyaluronic acid, collagen, poly(N-isopropyl acrylamide), amylose, cellulose, poly(hydroxybutyrate), poly(lactic acid), poly(butylenesuccinate), poly(caprolactone), carboxymethylcellulose, dextran, and cyclodextrin.

Based on the objectives stated above, the present invention provides a pharmaceutical composition composed of chelating complex micelles, which contains at least one block copolymer, at least one drug molecule, and at least one metal. The block copolymer, which acts as a Lewis base, contains a chelating segment for coordinate bonding and a neutral segment for better dispersion in biological fluids. The drug with a functional group that can donate a lone pair of electrons is considered as a Lewis base. Metal ions, which are invariably complexed with additional ligands, are often sources of coordinatively unsaturated derivatives that form Lewis adducts upon reaction with a Lewis base. The metal ion mentioned above can be ferrous ($Fe^{2+}$), ferric ($Fe^{3+}$) or gadolinium ($Gd^{3+}$); and the drug can be amifostine or WR-1065; and the block copolymer is poly(ethylene glycol)-b-poly(glutamic acid) (PEG-b-PGA). The PGA is designed for chelating segment while PEG is the neutral segment used for enhancing dispersity in aqueous solution.

Based on the objectives stated above, the present invention provides a method for preparing the pharmaceutical composition composed of chelating complex micelles. The raw materials include amifostine, PEG-b-PGA block copolymer, and ferrous chloride $FeCl_2$. After well mixing in a buffer solution, amifostine, ferrous ion ($Fe^{2+}$) and PEG-b-PGA block copolymer self-assembled to form the complex micelles via coordinate bonding. The amounts of the reactants used are: amifostine 0.1-10 mg, PEG-b-PGA 0.1-100 mg, and $FeCl_2$ 0.01-50 mg. The concentration of amifostine is around 0.01-10 mg/mL, and the buffer can be HEPES [4-(2-hydroxyethyl)-1-piperazinee-thanesulfonic acid)], with a pH value of 6.5 to 7.5. The temperature of the reaction is 4-40° C.

DETAILED DESCRIPTION OF THE EMBODIMENTS

Figure 1:
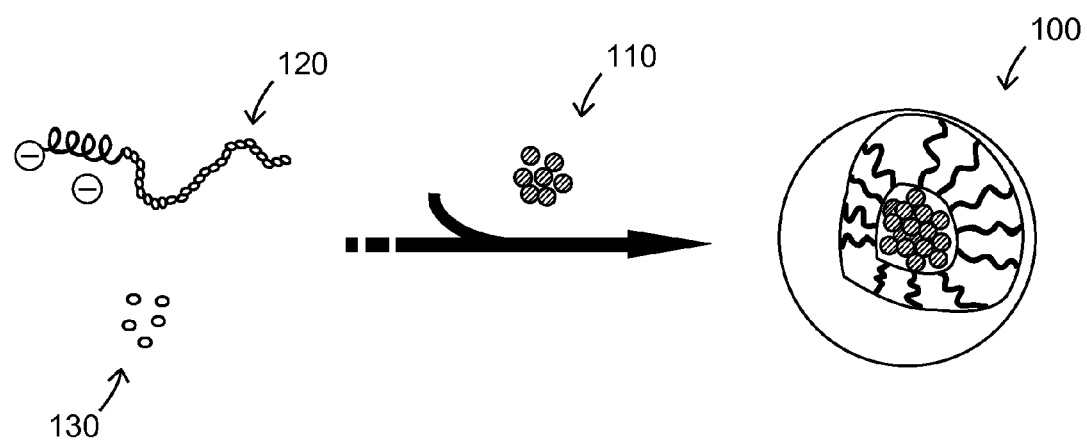
FIG. 1 shows the schematic diagram of the production method for a pharmaceutical composition composed of chelating complex micelles; it is based on the third example of the present invention.

The present invention is directed to drug carriers. In order to facilitate a thorough understanding of the present invention, detailed structures, their elements and methods will be provided in the following descriptions. The implementations of the present invention are not limited to specific details familiar to those engaged in and with full knowledge of drug carrier. On the other hand, widely known structures and their elements are omitted herein to avoid unnecessary limitations on the present invention. In addition, for better understanding and clarity of the description by those skilled in the art, components in the figures are not necessarily drawn to scale;

some scales may be exaggerated relative to others, and irrelevant parts are not completely presented to provide a simpler and clearer figure. Preferred embodiments of the present invention are described in details below. In addition, the present invention can be widely applicable to other embodiments, and the scope of the present invention is not limited by such rather by the scope of the following claims.

According to the invention of the first embodiment, the present invention provides a drug carrier composed of chelating complex micelles; the chelating complex micelles contain a metal ion core and at least one ligand. The metal ion is a Lewis acid that interacts with the ligands through coordinate bonds. The metal is selected from the following lists, either as single one, its derivative, or any combinations thereof: Fe, Cu, Ni, In, Ca, Co, Cr, Gd, Al, Sn, Zn, W, Sc, Ti, Mn, V, Mg, Be, La, Au, Ag, Cd, Hg, Pd, Re, Tc, Cs, Ra, Ir, and Ga. The ligand is selected from the following lists, either as single one, its derivatives or any combination thereof: carboxylic acids, alcohols, ketones, furans, amines, anilines, pyrroles, thiols, esters, amides, imines, pyridines, pyrimidines, imidazoles, pyrazols, sulfonamides, and phosphonic acids.

Chelating complex micelles use the metal ion as a core and conjugate the drug molecule, which acts as a Lewis acid, via coordinate bonds. The drug Lewis base donates lone pairs of electrons in the coordinate bonding formation, and is selected from the following lists, either as single one, its derivatives or any combination thereof: amifostine, WR-1065, doxorubicin, pemetrexed, gemcitabine, methotrexate, docetaxel, vinblastine, epirubicin, topotecan, irinotecan, ifosfamide, gefitinib, erlotinib, penicillin class, cloxacillin, dicloxacillin, gentamicin, vancomycin, amphotericin, quinolones, piperazine, fluoroquinolone, nalidixic acid, ciprofloxacin, levofloxacin, trovafloxacin, oseltamivir, metformin, trastuzumab, imatinib, rituximab, bevacizumab, celecoxib, etodolac, ibuprofen, cyclosporine, morphine, erythropoietin, granulocyte colony-stimulating factor, curcumin (enol, keto form), glutathione, Vitamin C, acetylcysteine, carnitine, galantamine, insulin, imipenem, cilastatin, ertapenem, meropenem, entecavir, telbivudine, lamivudine, melatonin, tocopherols, tocotrienol (Vitamin E), L-carnitine, carotenes, ubiquinol, lipoic acid, polyphenols, catecholamine, resveratrol, piceid, tempo, asarone, aminoguanidine, tocopherol monoglucoside, glycyrrhizic acid, epicatechin, flavonoid, orientin, vicenin, MPG (2-mercaptopropionyl glycine), and Mesna (2-mercaptoethanesulfonic acid).

According to the invention of the second embodiment, the invention provides a drug carrier composed of chelating complex micelles; the chelating complex micelles contain a metal ion core, at least one polymer, and at least one drug molecule. The metal ion is considered as a Lewis acid while polymer chain and drug molecules are referred to as Lewis bases. The Lewis bases (polymer chains and drug molecules) provide lone pairs of electrons and conjugate to metal Lewis acid via coordinate bonding.

The polymer mentioned above can be monodentate (unidentate) ligands, bidentate ligands, the tridentate ligands, hexadentate ligands, and polydentate ligands, with molecular weight in the range of 1,000-50,000 Dalton. The polymer is selected from the following lists, either as single one, its derivatives or any combinations thereof: poly (ethylene glycol), polyaspartic acid, polyglutamic acid, polylysine. poly (acrylic acid), chitosan, polyethylenimine, poly(methacrylic acid), hyaluronic acid, collagen, poly(N-isopropyl acrylamide), amylose, cellulose, poly(hydroxybutyrate), poly(lactic acid), poly T(butylenesuccinate), poly(caprolactone), carboxymethyl cellulose, dextran, and cyclodextrin.

In addition, the selection criterion of drug Lewis base that donates lone pairs of electrons for the second embodiment is as same as the first embodiment. The selection criterion of metal Lewis acid is also similarly described in the first embodiment.

According to the invention of the third embodiment, the invention provides a pharmaceutical composition composed of chelating complex micelles for biomedical applications, such as cell protective agent. The chelating complex micelles contain a metal ion core, at least one block copolymer and at least one drug molecule. The metal ion is considered as a Lewis acid while block copolymers and drug molecules are referred to as Lewis bases. The Lewis bases (block copolymers and drug molecules) provide lone pairs of electrons and conjugate to metal Lewis acid via coordinate bonding.

The aforementioned metal ion includes an Fe (iron) or Gd (gadolinium) ion; the aforementioned drugs includes amifostine or WR-1065; and the aforementioned block copolymer possesses one chelating segment that can form coordinate bonds with metal ions, while the other end is the neutral segment used for enhancing dispersity in aqueous solution. An example of the block copolymer is poly(ethylene glycol)-b-poly(glutamic acid) (PEG-b-PGA). The PGA segment with excellent biocompatibility possesses carboxyl groups ($—COO^-$) that can form coordinate bonds with metal ions. On the other hand, the hydrophilic and neutral characteristics of the PEG segment makes the micelles well dispersed in biological fluids. It is worth noting that PEG does not provide any functional groups for coordinate bonding. Appropriate modification is necessary to allow it to possess chelating ability. The PGA segment, which is a biodegradable polypeptide, is also used to link PEG and metal ions.

The aforementioned drugs include amifostine or WR-1065. Amifostine has five functional groups that can donate lone pairs of electrons, i.e., two —OH, one each of —P=O, NH and —$NH_2$; WR-1065 has three available, one each of —SH, —NH and —$NH_2$.

As illustrated in FIG. 1, the production of pharmaceutical composition (designated as 100) encompassing the chelating complex micelles is as follows. Mix continuously 0.1-10 mg cytoprotective agent, amifostine (designated as 110), 0.1-100 mg PEG-b-PGA (designated as 120) and 0.01-50 mg $FeCl_2$ (designated as 130) in 1-10 mL buffer solution at 4-40° C. for up to 48 hours. Based on the aforementioned bonding principle, amifostine (designated as 110), PEG-b-PGA (designated as 120), and ferrous ion ($Fe^{2+}$) (designated as 130) self-assembled to form chelating complex micelles with diameter around 10-300 nm. This chelating complex micelle is designated as cytoprotective agent (designated as 300). The buffer solution can be 0.05 M HEPES (4-(2-hydroxyethyl)-1-piperazineethane-sulfonic acid) with a pH 6.5-7.5.

Figure 2A:
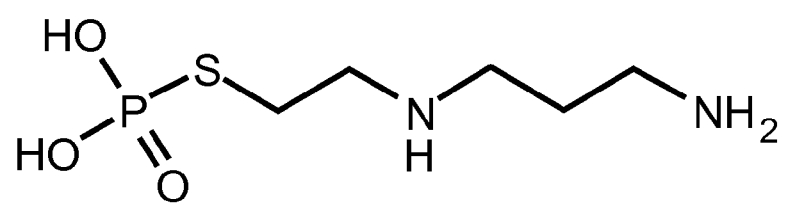
FIGS. 2A and 2B show the structures of amifostine and its derivative WR-1065 of the present invention.
Figure 2B:
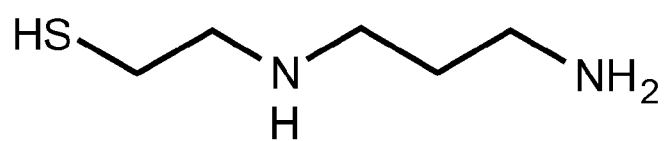
Figure 3:
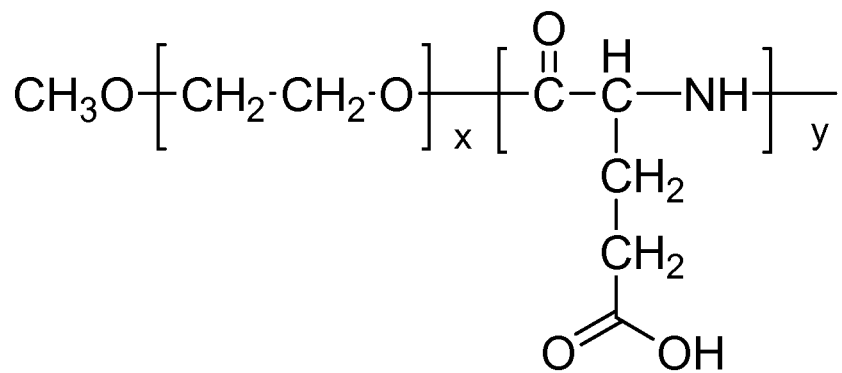
FIG. 3 shows the structure of block copolymer poly(ethylene glycol)-b-poly(glutamic acid) of the present invention.
Figure 4:
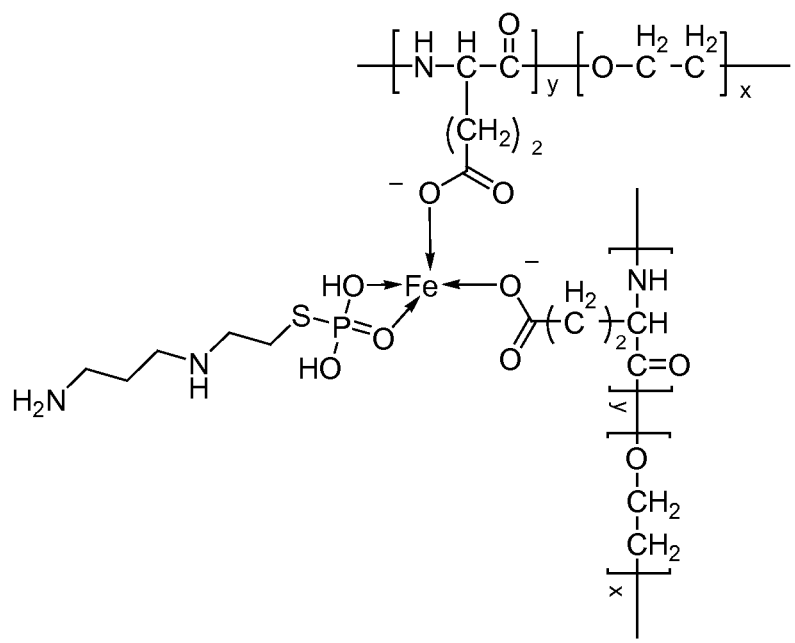
FIG. 4 shows the schematic diagram of chelating complex micelles loaded with cytoprotective agent amifostine of the present invention.
Figure 5:
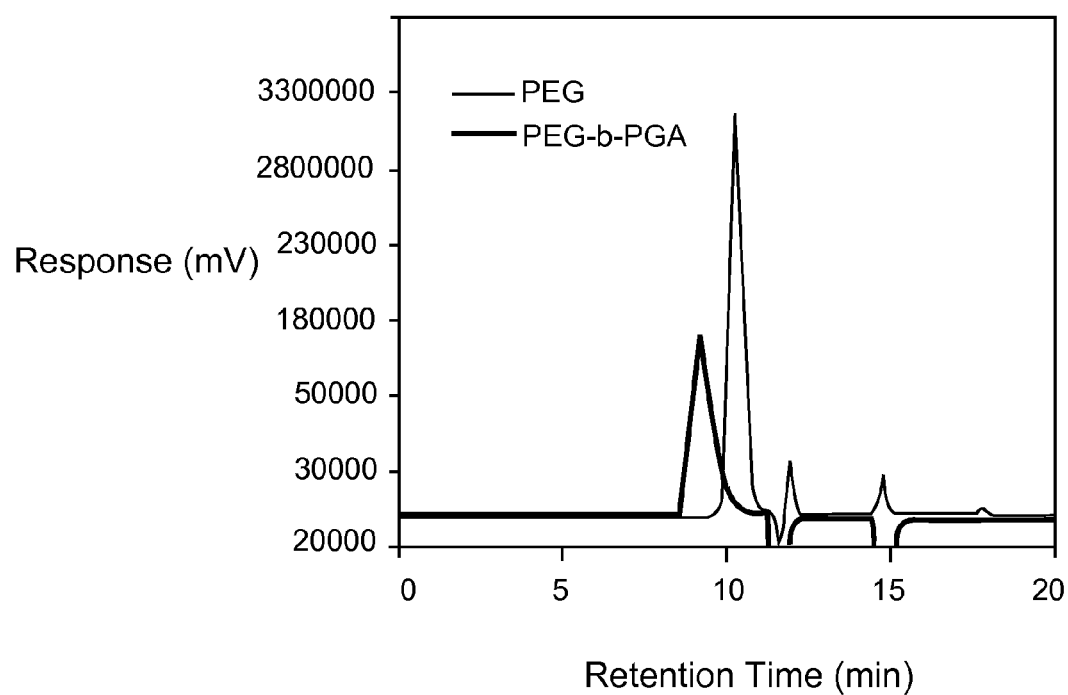
FIG. 5 shows the GPC (gel permeation chromatography) analysis diagram for PEG and PEG-b-PGA.
Figure 6:
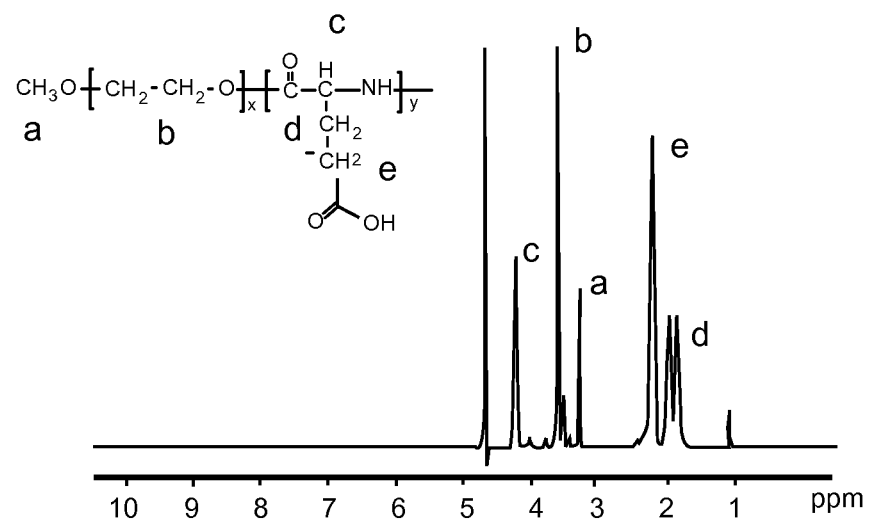
FIG. 6 shows the $^1$H-NMR spectrum with corresponding chemical shift of PEG-b-PGA.
Figure 7:
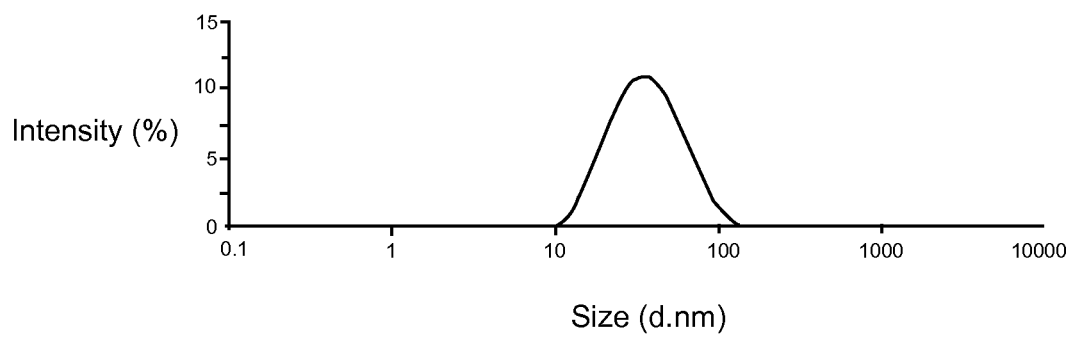
FIG. 7 shows the size distribution of chelating complex micelles determined by DLS (dynamic light scattering)

FIGS. 2A and 2B show the structures of amifostine and its derivative WR-1065. FIG. 3 shows PEG-b-PGA. FIG. 4 shows the structure of chelating complex micelles loaded with cytoprotective agent amifostine. In this embodiment, PEG-b-PGA is synthesized using PEG as a macroinitiator. The analysis result of GPC (gel permeation chromatography) is shown in FIG. 5. The $M_w$ (weight-average molecular weight), $M_n$ (number-average molecular weight), and PdI (polydispersity index) are 5700, 4900, and 1.16, respectively. FIG. 6 shows the $^1$H-NMR spectrum with corresponding chemical shift of PEG-b-PGA. FIG. 7 shows the size distribution of chelating complex micelles determined by DLS (dynamic light scattering), which indicates that the Z-average diameter is 31.61 nm.

Figure 8:
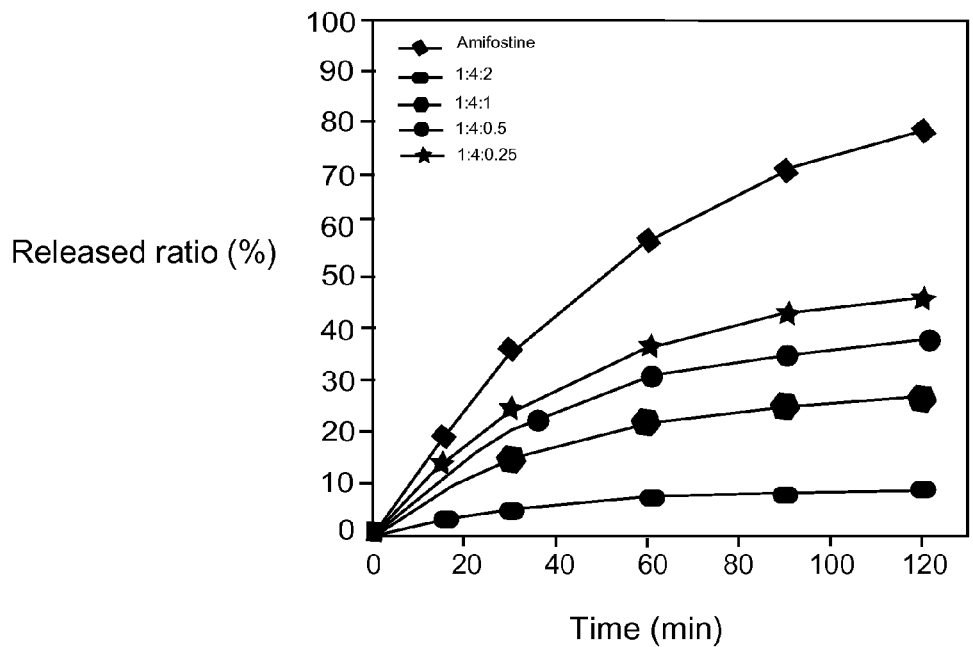
FIG. 8 shows the in vitro released profiles of amifostine and amifostine-loaded CCM. The release ratio is decreased as increasing the amount of $FeCl_2$.

FIG. 8 shows the in vitro released profiles of amifostine and amifostine-loaded CCM. Five milligrams of amifostine, 20 mg of PEG-b-PGA ($M_w$ 5700 Dalton), and 1.25-10 mg of $FeCl_2$ (weight ratio from 1:4:0.25 to 1:4:2) are continuously mixing in 5 mL of buffer solution at 25° C. for 24 hours. The mixture is placed in a dialysis tube (with a molecular weight cut off 3500) and soaked in water to simulate the drug release. The results show that with 10 mg of $FECl_2$ (weight ratio 1:4:2), most of amifostine are trapped in the chelating complex micelles and cannot diffuse through the dialysis membrane. The release ratio is decreased as increasing the amount of $FECl_2$. The above buffer solution is 0.05 M HEPES (4-(2-hydroxyethyl)-1-piperazineethane sulfonic acid), pH 7.0.

Figure 9:
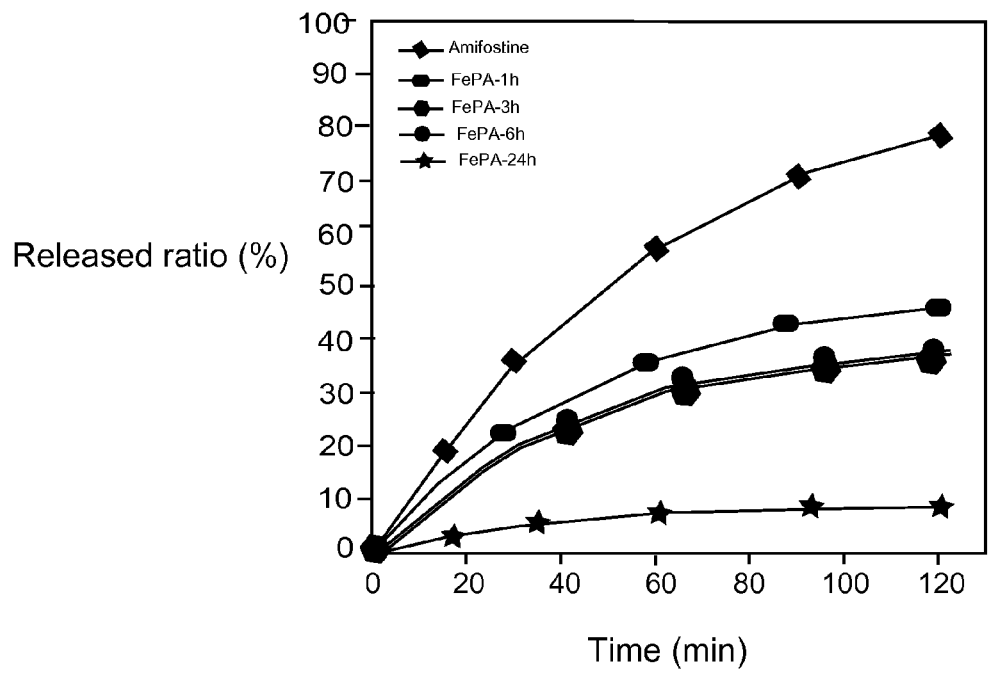
FIG. 9 shows the in vitro released profiles of amifostine and amifostine-loaded CCM. The release ratio is decreased as increasing the reaction time.

FIG. 9 shows the in vitro released profiles of amifostine and amifostine-loaded CCM. Five milligrams of amifostine, 20 mg of PEG-b-PGA ($M_w$ 5700 Dalton), and 10 mg of $FECl_2$ (weight ratio 1:4:2) are continuously mixing in 5 mL of buffer solution at 25° C. with various reaction time. The mixture is placed in a dialysis tube (with a molecular weight cut off 3500) and soaked in water to simulate the drug release. The results show that after 24 hours of reaction, most of amifostine are trapped in the chelating complex micelles and cannot diffuse through the dialysis membrane. The release ratio is decreased as increasing the reaction time. The above buffer solution is 0.05M of HEPES (4-(2-hydroxyethyl)-1-piperazineethanesulfonic acid), pH 7.0.

In general, drug molecules are difficult to link to polymers in order for specific purposes. By the concept of coordinate bonding provided from the present invention, the metal Lewis acid, which can combine with drugs and polymers to form chelating complex micelles at the same time. Such micelles not only possess the structure similar to the chelating agent EDTA, but also prolong the half-life of drugs in the human body, and not causing human toxicity (EDTA will bind the metal elements in the body). In addition, the coordinate bonding can also overcome the weak interaction provided by ionic bonding. On the other hand, metal ions may precipitate under aqueous conditions as interacting with oxidants. Although PEG shows very good dispersion property in the aqueous solution but has no functional group to conjugate with other substances. Thus, PEG must be modified through introducing the PGA segment to chelate metal ions, and prevent the precipitation of metal ions. It is worth noting that the carrier of the present invention can be applied to either hydrophilic or hydrophobic drugs, thus greatly enhancing its application value. In addition, the FDA approved API (active pharmaceutical ingredient) may be regarded as a new drug if functional groups are changed. The safety and efficacy must be re-validated, thus demanding extremely high capital investment. In contrast, the present invention is completely without any changes on the structure of drug and therefore will not raise the problem of re-validation. Consequently, for the processing compatibility, the present invention is exceptionally valuable.

It is apparent that based on the above descriptions of the embodiments, the present invention may have numerous modifications and alterations, and they should be construed within the scope of the following claims. In addition to the above detailed descriptions, the present invention can be widely applied to other embodiments. The above embodiments are merely preferred embodiments of the present invention, and should not be used to limit the present invention in any way. Equivalent modifications or changes made without departing from the principles of the present invention must be included in the following scope of the patent claims.

Explanation of The Symbols for The Major Elements
100 Pharmaceutical composition composed of chelating complex micelles
110 cytoprotective agent amifostine
120 block copolymer poly(ethylene glycol)-b-poly(glutamic acid) (PEG-b-PGA)
130 ferrous chloride ($FECl_2$)

What is claimed is:

1. A chelating complex micelle, comprising:
   a ligand free metal ion core, wherein the ligand free metal ion core is a Lewis acid; and
   a ligand, wherein the ligand and the ligand free metal ion core bind to each other by coordinate bonds;
   wherein said ligand free metal ion core links a drug wherein the ligand is poly(ethylene glycol)-b-poly(glutamic acid) (PEG-b-PGA).

2. The chelating complex micelle of claim 1, wherein the ligand free metal ion core is selected from the following lists: either single one or any combination thereof: Fe, Cu, Ni, In, Ca, Co, Cr, Gd, Al, Sn, Zn, W, Sc, Ti, Mn, V, Mg, Be, La, Au, Ag, Cd, Hg, Pd, Re, Tc, Cs, Ra, Ir, and Ga.

3. The chelating complex micelle of claim 1, wherein the ligand is selected from the following lists: either single one or any combination thereof: carboxylic acids, alcohols, ketones, furans, amines, anilines, pyrroles, thiols, esters, amides, imines, pyridines, pyrimidines, imidazoles, pyrazols, sulfonamides, and phosphonic acid.

4. The chelating complex micelle of claim 1, wherein the drug is a Lewis base drug.

5. The chelating complex micelle of claim 4, wherein the Lewis base drug contains one or more functional groups, which are selected from the following groups of carboxylic acids, alcohols, ketones, furans, amines, anilines, pyrroles, thiols, esters, amides, imines, pyridines, pyrimidines, imidazoles, pyrazols, sulfonamides, phosphonic acids, and any combination thereof.

6. The chelating complex micelle of claim 4, wherein the Lewis base drug is selected from the following groups of amifostine, WR-1065, doxorubicin, pemetrexed, gemcitabine, methotrexate, docetaxel, vinblastine, epirubicin, topotecan, irinotecan, ifosfamide, gefitinib, erlotinib, penicillin class, cloxacillin, dicloxacillin, gentamicin, vancomycin, amphotericin, quinolones, piperazine, fluoroquinolone, nalidixic acid, ciprofloxacin, levofloxacin, trovafloxacin, oseltamivir, metformin, trastuzumab, imatinib, rituximab, bevacizumab, celecoxib, etodolac, ibuprofen, cyclosporine, morphine, erythropoietin, granulocyte colony-stimulating factor, curcumin (enol, keto form), glutathione, Vitamin C, acetylcysteine, carnitine, galantamine, insulin, imipenem, cilastatin, ertapenem, meropenem, entecavir, telbivudine, lamivudine, melatonin, tocopherols, tocotrienol (Vitamin E), L-carnitine, carotenes, ubiquinol, lipoic acid, polyphenols, catecholamine, resveratrol, piceid, tempo, asarone, aminoguanidine, tocopherol monoglucoside, glycyrrhizic acid, epicatechin, flavonoid, orientin, vicenin, MPG (2-mercaptopropionyl glycine), Mesna (2-mercaptoethanesulfonic acid), and any combination thereof.

* * * * *